(12) United States Patent
Kuo et al.

(10) Patent No.: US 8,740,118 B2
(45) Date of Patent: Jun. 3, 2014

(54) PORTABLE GRINDING DEVICE

(75) Inventors: Shih-Hung Kuo, New Taipei (TW); Bruce Lai, Taipei (TW)

(73) Assignee: Rega Biotechnology Inc., New Taipei (TW)

( * ) Notice: Subject to any disclaimer, the term of this patent is extended or adjusted under 35 U.S.C. 154(b) by 369 days.

(21) Appl. No.: 13/311,598

(22) Filed: Dec. 6, 2011

(65) Prior Publication Data

US 2013/0008988 A1 Jan. 10, 2013

(30) Foreign Application Priority Data

Jul. 7, 2011 (TW) .............................. 100212417 U

(51) Int. Cl.
*B02C 17/10* (2006.01)
(52) U.S. Cl.
USPC .......................................... 241/168; 241/179
(58) Field of Classification Search
CPC ........ B02C 17/18; B02C 17/10; B02C 17/14; B02C 17/182
USPC ........... 241/2, 168, 169, 169.2, 179, 184, 175
See application file for complete search history.

(56) References Cited

U.S. PATENT DOCUMENTS

| | | | | |
|---|---|---|---|---|
| 1,531,651 | A * | 3/1925 | Geiger | 241/30 |
| 6,880,771 | B2 * | 4/2005 | Deppermann | 241/2 |
| 8,348,183 | B2 * | 1/2013 | Mertens et al. | 241/2 |

* cited by examiner

*Primary Examiner* — Mark Rosenbaum
(74) *Attorney, Agent, or Firm* — Bacon & Thomas, PLLC

(57) ABSTRACT

A grinding device, comprising a body configured as a hollow barrel having an opening and a first fixing element positioned close to the opening; an inner cap configured to mount to an inner wall of an end close to the opening of the body having a second fixing element corresponding to the first fixing element; wherein an aperture is provided on the inner cap, and a first leak-proof seal is configured to surround the aperture; an outer cover having a second leak-proof seal, wherein the second leak-proof seal engages the first leak-proof seal for leak-proofing; and a grinding element positioned inside the body and capable of moving therein freely; wherein an area of any cross section of the grinding element is bigger than the aperture of the inner cap.

8 Claims, 7 Drawing Sheets

PORTABLE GRINDING DEVICE

BACKGROUND OF THE INVENTION

1. Field of the Invention

The present invention is related to a grinding device; more particularly, the present invention is related to a grinding device for prompt test.

2. Description of the Related Art

As prompt tests are getting more and more attention in nowadays, several tests (such as tests for allergens) are gradually conducted in people's daily life. For any test, no matter the sample to be tested is an animal material or a plant material, it is required to grind the sample before proceeding to the test for well-mixing with chemical reagents used. Because the process of grinding samples significantly affects the efficiency and correction of tests, the development of a portable grinding device is necessary in order to conveniently grind samples for proceeding basic tests in daily life.

Take tests for determining allergens in foods as an example. Allergy is considered as an adverse reaction that a body response to a specific substance. It is said that a body must contact such substance at least once before and an allergic reaction may be induced as the body contacts the substance thereafter. When an allergic reaction is induced, immunoglobulins (e.g. IgE) will react with the substance concerned and release histamine, which is the key chemical substance relevant to allergy-based diseases or symptoms such as hay fever, asthma, itch, dyspnea, stomachalgia, vomiting and diarrhea.

Food-induced allergy is very common in allergic mechanisms. Almost more than 90% of food-induced allergy results from milk products, egg, barley, soy bean, peanut, fishes or crustaceans; wherein egg, milk product and peanut are the most common allergy source, and peanut, fishes and crustaceans often induce the most severe allergic reaction. It is record that about 3% of the child population suffers different kinds of food allergy. Although most children may get rid of allergy when they grow up, some of them may suffer from allergy of peanut or crustaceans often last for their whole life.

Symptoms of allergy may occur within several minutes to several hours after food intake. Common symptoms thereof include vomiting, diarrhea, abdominal pain, urticaria, tumefaction, eczema, itch in lip or oral, itch or tightness in throat, dyspnea, asthma, low blood pressure, etc.

According to information from National Institute of Allergy and Infectious Diseases in U.S.A., it is not necessary to have a large amount of food for people with hyper-allergy to induce severe allergic reaction. In fact, only an amount of $\frac{1}{44000}$ of the weight of a single peanut may induce severe allergic reaction for those people.

There is no medicine for preventing food allergy. The only way to prevent allergy is to avert from eating food that may induce allergy. Once certain foods are diagnosed to induce allergy for your kid, it is very important to avoid not only those foods but also the relevant foods. If a kid is fed with mother's milk, the mother shall also avoid eating such food. Allergic food may transfer into child's body through mother's milk and induce allergic reaction even if at an extremely low amount.

With advances in technology, the percentage of various processed foods in human daily diet is getting higher and higher. Meanwhile, it is hard to learn the original raw materials of those processed foods by observing the appearance thereof. Although it is asked to clearly indicate the contents thereof on the package of those processed food, the customers can only choose to trust the labeled information. After all, it is impossible for them to forward every processed food to a testing center because of economic consideration. Thus, the development of a testing device that can be easily performed at home is favorable for people with hyper-allergy to eat healthier and more safely.

To sum up, not only for allergy test, but also for properly grinding animal or plant materials in daily life, a portable and efficient grinding device is constantly in need.

SUMMARY OF THE INVENTION

To better appreciate the long and expensive testing procedure that has to conduct by testing centers, one object of the present invention is to develop a grinding device for grinding samples. By cooperating with testing kits, a person in need can conduct a test for identification promptly by itself.

To achieve the above objects, the present invention provides a grinding device, comprising: a body configured as a hollow barrel having an opening, a first fixing element positioned close to said opening and an external thread configured on an outer wall of an end close to said opening of said body; an inner cap configured to mount to an inner wall of an end close to said opening of said body having a second fixing element corresponding to said first fixing element; wherein said second fixing element is configured to anchor with said first fixing element; wherein an aperture is provided on said inner cap, and a first leak-proof seal is configured to surround said aperture; an outer cover having an inner thread, a second leak-proof seal and a projection; wherein said inner thread is configured to lock with said external thread of said body, and thereby said second leak-proof seal is made joint said first leak-proof seal for leak-proofing; and a grinding element positioned inside said body and capable of moving therein freely; wherein an area of any cross section of said grinding element is bigger than said aperture of said inner cap.

The present invention can effectively crush the samples for test, and thereby make the test kits cooperated therewith more sensitive in reaction and identification.

DETAILED DESCRIPTION OF THE PRESENT INVENTION

Figure 1:
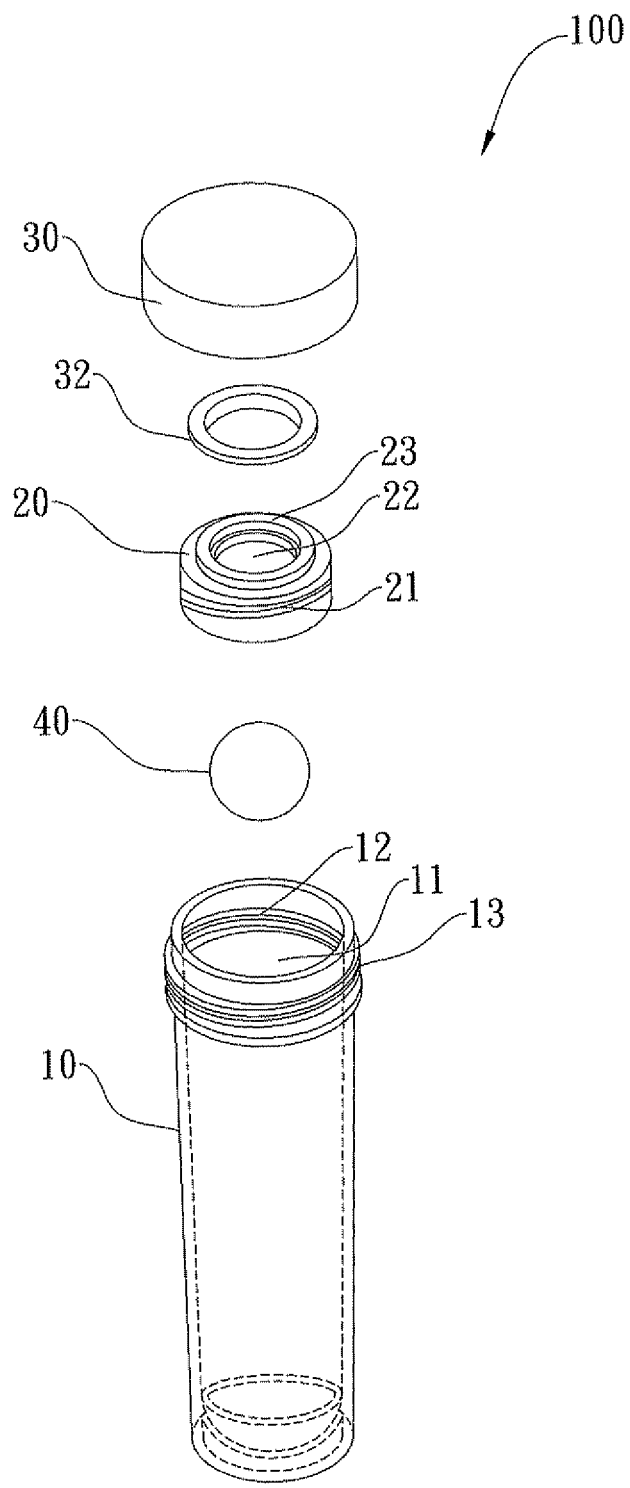
FIG. 1 is an exploded view of the grinding device of the present invention showing all elements thereof.

The grinding device 100 of the present invention can be understood by referring to FIGS. 1, 2B, 3A and 3B; wherein said grinding device 100 comprises a body 10 configured as a hollow barrel having an opening 11, a first fixing element 12 positioned close to said opening 11 and an external thread 13 configured on an outer wall of an end close to said opening 11 of said body 10; an inner cap 20 configured to mount to an inner wall of an end close to said opening 11 of said body 10 having a second fixing element 21 corresponding to said first fixing element 12; wherein said second fixing element 21 is configured to anchor with said first fixing element 12; wherein an aperture 22 is provided on said inner cap 20, and a first leak-proof seal 23 is configured to surround said aperture 22; an outer cover 30 having an inner thread 31, a second leak-proof seal 32 and a projection 33; wherein said inner thread 31 is configured to lock with said external thread 13 of said body 10, and thereby said second leak-proof seal 32 engages the first leak-proof seal 23 for leak-proofing; and a grinding element 40 positioned inside said body 10 and capable of moving therein freely; wherein an area of any cross section of said grinding element 40 is bigger than said aperture 22 of said inner cap 20.

Figure 2A:
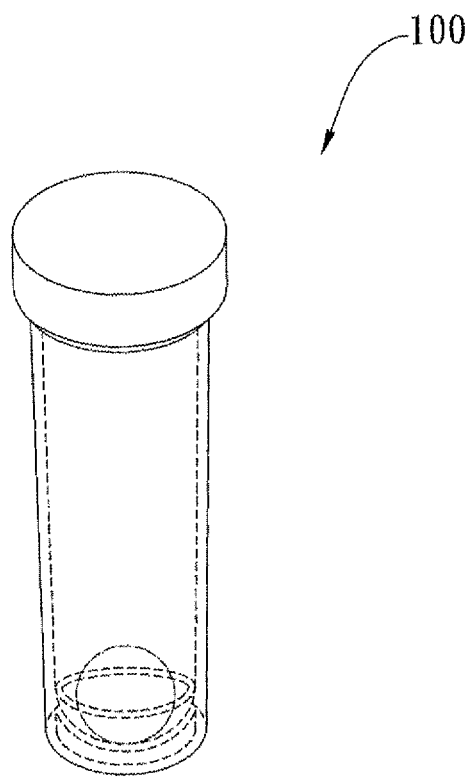
FIG. 2A shows the appearance of the grinding device of the present invention after assembling all elements thereof.
Figure 2B:
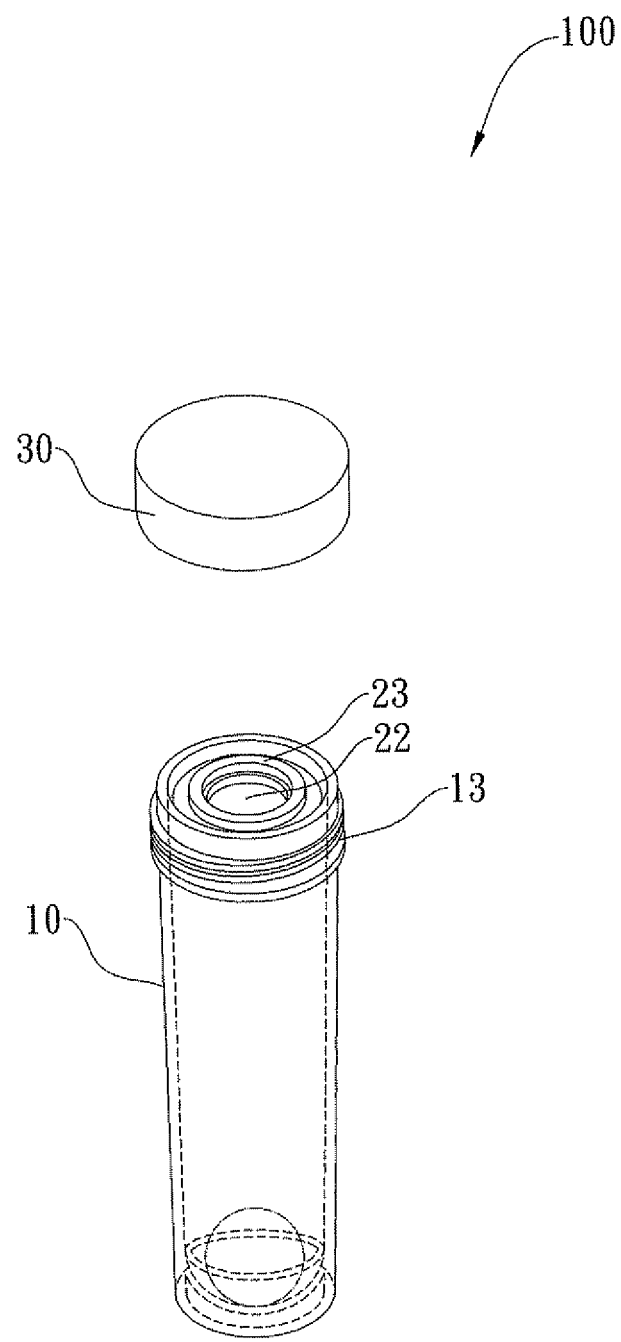
FIG. 2B shows the appearance of the grinding device of the present invention while the outer cover is opened.

FIG. 2A shows the appearance of the grinding device after assembling all elements thereof, and FIG. 2B shows the appearance under the circumstance that said inner cap 20, said grinding element 40 and said body 10, but said outer cover 30, have been assembled together. For normal usage, the closed grinding device 100 of the present invention such as showed in FIG. 2A is first opened as showed in FIG. 2B. A sample and reagents are applied into said grinding device 100 and then said body 10 and said outer cover 30 is locked with each other tightly as showed in FIG. 2A. After that, said body 10 of said grinding device 100 is shaken hardly to let said grinding element 40 move inside the internal space of said body 10 and crush the sample for mixing with the reagents.

Figure 3A:
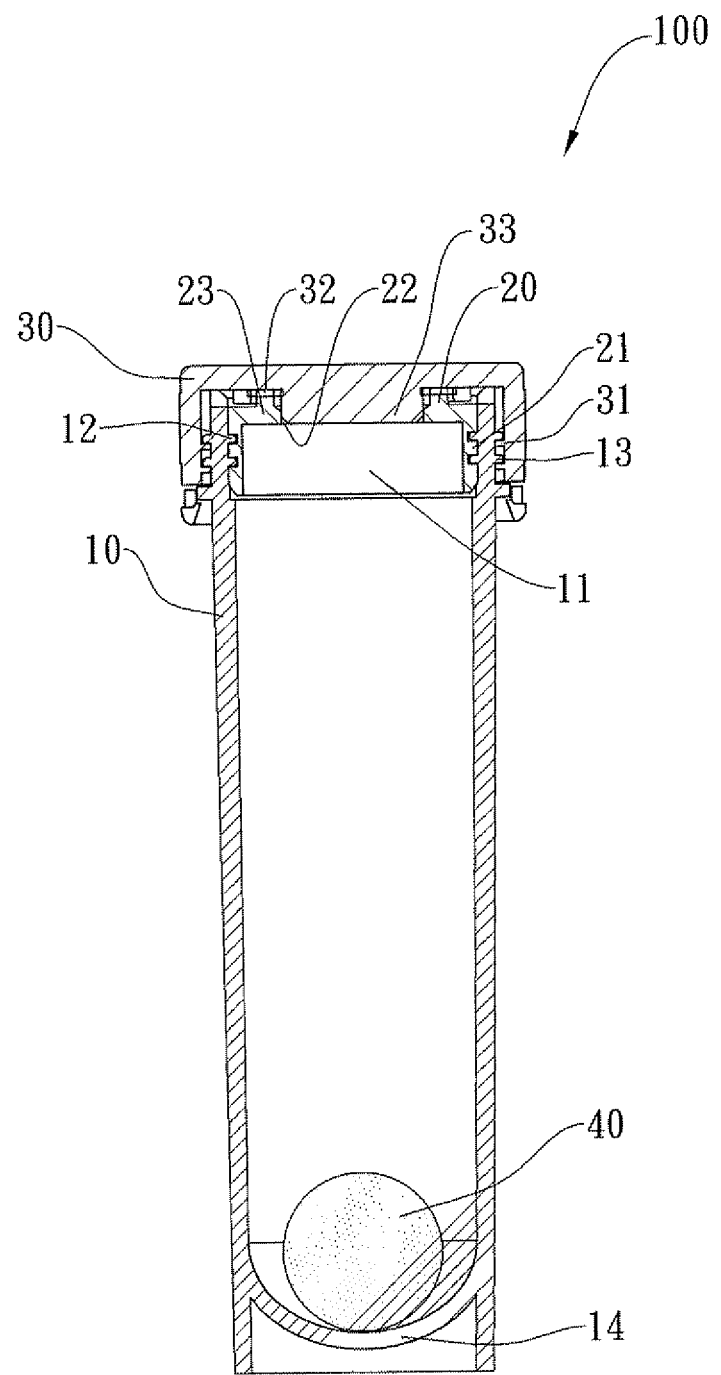
FIG. 3A is a section view of the structure of the grinding device of the present invention.
Figure 3B:
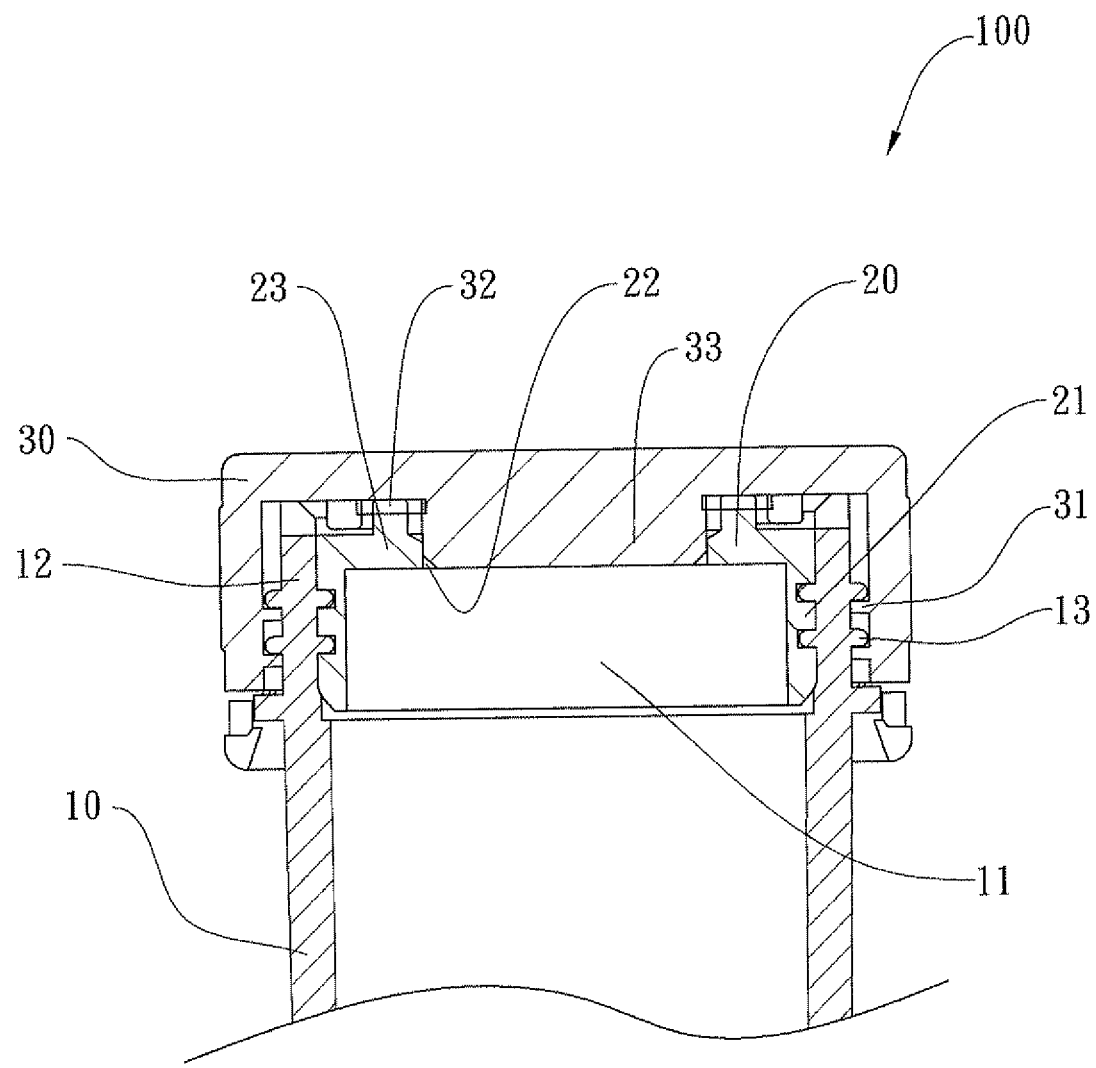
FIG. 3B is a section view of the partial structure of the grinding device of the present invention.

Please refer to the prefer embodiment in FIG. 3A, wherein the bottom of said body 10 is configured to form a central recess 14. The inner surface of said central recess 14 substantially matches with the outer surface of said grinding element 40. By such configuration, the contact area between said grinding element 40 and said body 10 while said grinding element 40 is crushing downward can be enlarged to improve the mixing efficiency. More specifically, when said grinding element 40 is moving inside said body 10, it is continuously colliding with the wall of said body 10, said central recess 14 and said projection 33. Consequently, the sample positioned inside said body 10 is ground and crushed effectively.

Accordingly, in a prefer embodiment, said body 10 is in a shape of a hollow drum such as showed in FIG. 1 and said grinding element 40 is a ball; therefore, no dead space is existed between said body 10 and said grinding element 40, and thereby the sample can be mixed well with said reagents.

In an alternative embodiment as showed in FIG. 1, said first fixing element 12 is an inner thread, and said second fixing element 21 is an external thread. Said inner cap 20 and said body 10 are anchored together through the screwing-action between the inner thread and the external thread.

Figure 4:
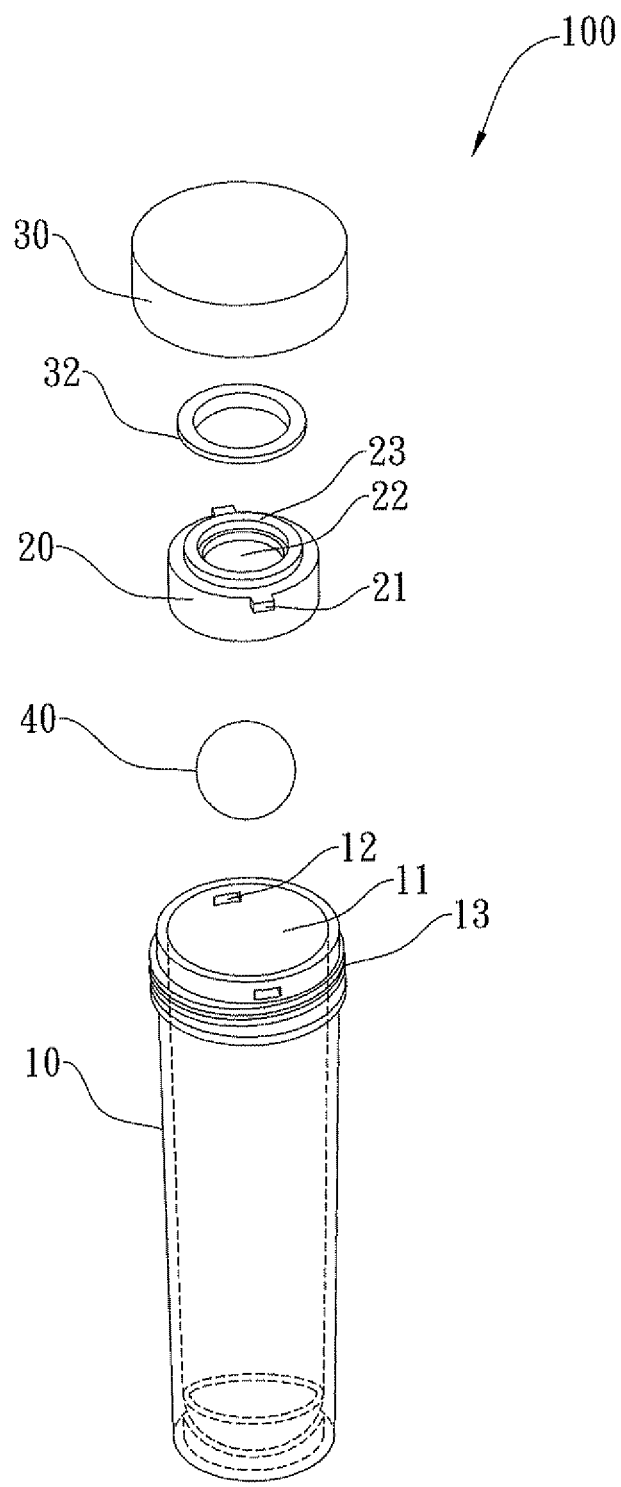
FIG. 4 is an exploded view of another embodiment of the grinding device of the present invention showing all elements thereof.

In an alternative embodiment as showed in FIG. 4, said first fixing element 12 is a clasp portion, and said second fixing element 21 is a clasp engaging portion. Said inner cap 20 and said body 10 are anchored together through the snapping-fit between the clasp portion and clasp engaging portion.

Figure 5:
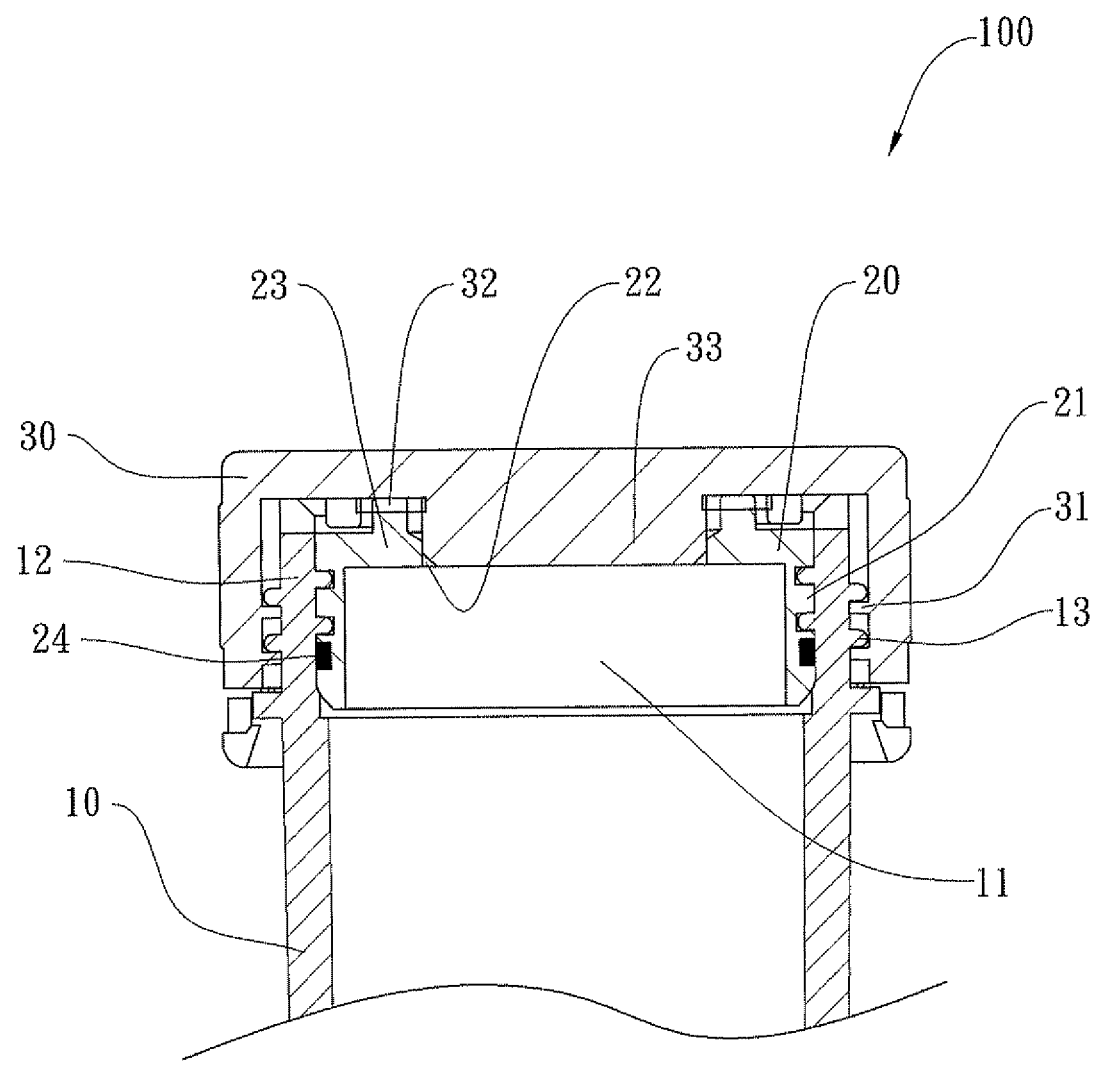
FIG. 5 is a section view of the partial structure of another embodiment of the grinding device of the present invention.

In an alternative embodiment as showed in FIG. 5, a gasket ring 24 is further configured at a site where said body 10 and said inner cap 20 are anchored with each other. Said gasket ring 24 is used for sealing so as to prevent the reagents in said body 10 from being leaking out from the site where said body 10 and said inner cap 20 are anchored with each other while using said grinding device 100.

In an alternative embodiment, said first leak-proof seal 23 of said inner cap 20 is a convex part and said second leak-proof seal 32 of said outer cover 30 is a pad, vice versa; which means, on the other hand, said first leak-proof seal 23 can be a pad positioned in said inner cap 20 and said second leak-proof seal 32 can therefore be a convex part positioned in said outer cover 30. While said outer cover 30 is locked with said body 10 through the connection between said inner thread 31 and said external thread 13, said convex part and said pad can contact tightly with each other and prevent from the leakage of the sample and reagents inside said body 10 from the interval between said inner cap 20 and said outer cover 30.

The key technical feature of the present invention is the arrangement of the structure thereof; therefore, the material of each element is not limited. It can be easily understood that said body and/or said inner cap is preferably made of transparent polymer materials, and thereby the condition and volume of the contents can be easily observed. Moreover, a scale line indicating volume can be marked on the outer wall of said body while said body is made of a transparent polymer material for indicating the volume of the contents inside by visual observation.

In addition, although the material of said grinding element is not limited, a material with high density is preferable; such as glass or metal. It is because that a material with high density can provide heavier mass, which therefore provides larger colliding power while operating the grinding device and thereby improves the crushed degree to the sample.

Furthermore, since said outer cover and said body of the present invention is anchored and locked with each other through the connection between the inner thread and the external thread, it is easily realized that solid granules or stripes may be formed on a surface of said outer cover where a user's hand is contact while performing the anchoring and locking action. Therefore, the frictional force is improved for operating by hand.

On the other hand, the critical technical feature of the present invention is the arrangement of the structure thereof; therefore, the application of the present invention is not limit to the allergy test of food. As long as grinding material promptly and easily is required, the grinding device of the present invention can be used. The aforesaid material is not limited to an animal material or a plant material.

The above-description is only exemplary embodiments of the present invention and does not tend to limit the scope of the present invention. All variations and modifications included in the scope of spirit of the present invention shall be involved in the following claims.

What is claimed is:

1. A grinding device, comprising:
   a body configured as a hollow barrel having an opening, a first fixing element positioned close to said opening, and an external thread configured on an outer wall of an end close to said opening of said body;
   an inner cap configured to mount to an inner wall of an end close to said opening of said body having a second fixing element corresponding to said first fixing element; wherein said second fixing element is configured to anchor with said first fixing element; wherein an aperture is provided on said inner cap, and a first leak-proof seal is configured to surround said aperture;
   an outer cover having an inner thread, a second leak-proof seal and a projection; wherein said inner thread is configured to lock with said external thread of said body, and thereby said second leak-proof seal is made joint said first leak-proof seal for leak-proofing; and
   a grinding element positioned inside said body and capable of moving therein freely; wherein an area of any cross section of said grinding element is bigger than said aperture of said inner cap.

2. The device according to claim 1, wherein said body is configured as a hollow drum, and said grinding element is a ball.

3. The device according to claim 1, wherein said first fixing element is a clasp portion, and said second fixing element is a clasp engaging portion.

4. The device according to claim 1, wherein said first fixing element is an inner thread, and said second fixing element is an external thread.

5. The device according to claim 1, wherein a gasket ring is further configured at a site where said body and said inner cap are anchored with each other.

6. The device according to claim 1, wherein said first leak-proof seal is a convex part, and said second leak-proof seal is a pad.

7. The device according to claim 1, wherein said first leak-proof seal is a pad, and said second leak-proof seal is a convex part.

8. The device according to claim 1, wherein a bottom of said body has a central recess, and an inner surface of said central recess substantially matches with an outer surface of said grinding element.

* * * * *